(12) United States Patent
Turner et al.

(10) Patent No.: US 7,865,316 B2
(45) Date of Patent: Jan. 4, 2011

(54) SYSTEM, PROGRAM PRODUCT, AND RELATED METHODS FOR REGISTERING THREE-DIMENSIONAL MODELS TO POINT DATA REPRESENTING THE POSE OF A PART

(75) Inventors: Wesley Turner, Rexford, NY (US); James Miller, Clifton Park, NY (US); William Lorensen, Ballston Lake, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 54 days.

(21) Appl. No.: 12/202,016

(22) Filed: Aug. 29, 2008

(65) Prior Publication Data

US 2009/0248323 A1     Oct. 1, 2009

Related U.S. Application Data

(60) Provisional application No. 61/040,415, filed on Mar. 28, 2008.

(51) Int. Cl.
*G01B 5/30* (2006.01)
(52) U.S. Cl. .............................. 702/39; 702/33; 702/40; 356/432; 356/502; 73/655; 73/657
(58) Field of Classification Search .................... 702/33, 702/39, 40; 356/432, 502; 73/655, 657
See application file for complete search history.

(56) References Cited

U.S. PATENT DOCUMENTS

| | | |
|---|---|---|
| 2002/0048015 A1 | 4/2002 | Drake, Jr. |
| 2004/0154402 A1* | 8/2004 | Drake, Jr. .................... 73/621 |
| 2005/0102109 A1 | 5/2005 | Dubois |
| 2006/0215174 A1 | 9/2006 | Dubois et al. |

(Continued)

FOREIGN PATENT DOCUMENTS

EP     1813934 A1     8/2007

(Continued)

OTHER PUBLICATIONS

W Turner et al, Paper Titled "Using Computer Vision to Map Laser Ultrasound Onto CAD Geometries",GE Global Research, Oct. 2002.

(Continued)

*Primary Examiner*—Sujoy K Kundu
(74) *Attorney, Agent, or Firm*—Bracewell & Giuliani LLP (57) ABSTRACT

A system, program product, and method to perform automated three-dimensional image registration of a part within an inspection cell, are provided. The system can include a laser-ultrasound inspection device having a scanning head to generate ultrasonic surface displacements in a part, an inspection laser, and an interferometer to collect phase modulated light reflected by the part. The system can also include a part position locator positioned to measure a distance between points on a surface of the part and a scanning laser reference location. The system can also include a database containing computer-aided design models for each part of interest, and a model of the inspection cell. The system can further include a laser ultrasound inspection computer communication with the laser-ultrasound detection device and the part position locator, and laser ultrasound inspection program product adapted to perform automated three-dimensional image registration of the part.

25 Claims, 7 Drawing Sheets

U.S. PATENT DOCUMENTS

2006/0219014 A1 10/2006 Turner
2008/0016965 A1 1/2008 Drake

FOREIGN PATENT DOCUMENTS

GB 2311858 A 8/1997
WO 01/77613 A1 10/2001

OTHER PUBLICATIONS

C Basdogan, "From 2D Images to 3D Tangible Models: Autostereoscopic and Haptic Visualization of Martian Rocks in Virtual Environments," College of Engineering, Koc University, Istanbul, Turkey, Feb. 2008.

Besl, "A Method for Registration of 3D Shapes, IEEE Transactions on Pattern Analysis and Machine Intelligence" 14, pp. 239-256 (1992).

International Search Report and Written Opinion, Application No. PCT/US2009/038309, dated Aug. 25, 2009.

* cited by examiner

SYSTEM, PROGRAM PRODUCT, AND RELATED METHODS FOR REGISTERING THREE-DIMENSIONAL MODELS TO POINT DATA REPRESENTING THE POSE OF A PART

CROSS-REFERENCE TO RELATED APPLICATIONS

This non-provisional application claims priority to and the benefit of U.S. Provisional Patent Application No. 61/040,415, filed Mar. 28, 2008, titled " System, Program Product, and Related Methods for Registering Three-Dimensional Models to Point Data Representing the Pose of a Part."

BACKGROUND OF THE INVENTION

1. Field of the Invention

The present invention relates to three-dimensional scanning, and specifically to systems, program product, and methods to perform three-dimensional model registration.

2. Description of Related Art

In recent years, the use of various structures such as, for example, advanced composite structures have experienced tremendous growth in the aerospace, automotive, and many other commercial industries. While composite materials offer significant improvements in performance, they require strict quality control procedures in the manufacturing processes. Specifically, non-destructive evaluation ("NDE") methods are required to assess the structural integrity of the various structures, for example, to detect inclusions, delaminations and porosities. Conventional NDE methods, however, have traditionally been labor-intensive, and costly. As a result, testing procedures have adversely increased the manufacturing costs associated with composite structures.

Various systems and techniques have been proposed to assess the structural integrity of composite structures. Ultrasound testing, for example, has emerged as an extremely useful method of providing non-invasive, generally non-destructive, techniques used to measure various features of materials to include layer thickness, cracks, delamination, voids, disbonds, foreign inclusions, fiber fractions, fiber orientation and porosity. Such features influence a given material's qualities and performance in given applications. Each application of a structure places unique demands on the materials' structural qualities, including the need for differing strength, flexibility, thermal properties, cost, or ultraviolet radiation resistance. With the changing demands, more non-invasive, non-destructive testing of materials is being performed using techniques such as ultrasound testing. Ultrasound testing includes transducer-induced, laser, electromagnetic-induced and plasma-initiated ultrasound. Transducer-induced ultrasound techniques use piezoelectric transducers to induce an ultrasonic signal in an object.

Ultrasound techniques are applied in research as well as industrial settings. In research, ultrasound techniques are used to test new materials for desired features. The techniques are also used to seek defects in material that has undergone stress or environmental endurance testing. In industry, the techniques are used during scheduled servicing to inspect parts for defects. Aircraft, automobile, and other commercial industries have shown increasing interest in these techniques.

Wide area imaging devices also offer many speed and flexibility advantages to NDE applications. Such imaging devices can be reconfigured quickly to accommodate a variety of part geometries and sizes and can be deployed without precise fixturing for the sensor or the part. When the part to be inspected is large or complicated (with many bends), applications use several sensors or move a single sensor to multiple viewpoints to complete an inspection. An operator must then review several images for a single part, spatially relate indications across disparate images, and assume the collection of images completely covers the part.

Various non-destructive evaluation systems can use laser-ultrasound as a wide area, imaging device. Such systems can also use, for example, a three-dimensional scanner such as a structured light range camera to locate the part within a work cell. The three-dimensional scanner, for example, can create a point cloud of geometric samples ("point data") on the surface of the part. Such point data can represent the pose of a part in a given environment ("sensor data"). The point data is, however, usually not directly utilized. Camera calibration, photogrammetry, triangulation, and registration techniques are used to define coordinate frames that allow the system to relate the three-dimensional data from the laser-ultrasound imaging device to a computer-aided design ("CAD") model of the part. The system can then map the ultrasound data from various viewpoints onto the CAD model, creating a natural three-dimensional coordinate frame for the operator to relate indications and evaluate scan coverage.

Recognized by the Applicants, however, is that registration of three-dimensional models to point data representing the pose of a part is complicated by a combination of two fundamental characteristics of the sensor data. The first is the presence of outliers which are acquired as part of the sensor data, but that do not represent points on the model. These points can arise from noise in the sensor, or from other objects in the scene such as occluding surfaces, walls, tabletops, and etc. The second is the absence of data for sections of the model arising, perhaps, from places where the part was occluded or that were out of range of the sensor. Previous implementations circumvent this problem by prefiltering the data to remove outliers and/or by menu selection of the areas of the model and sensor data to use. Such techniques, however, reduce efficiency and increase the amount of time necessary to perform the registration, if registration is even possible.

An algorithm currently used to attempt to align such models includes the "Iterative Closest Point" algorithm. This algorithm works by selecting points in a source, calculating the closest point in the target to each of these points, and then calculating the transform which minimizes the distance between each point and its correspondence, and then applying this transform to the source moving it closer to the target. This process is repeated (iterated) until such time as the source and target are sufficiently close, a fixed number of iterations have been performed, or the registration has failed. Besl et al., "Method for Registration of 3-D Shapes," IEEE Transactions on Pattern Analysis and Machine Intelligence 14, pages 239-256 (1992), incorporated by reference in its entirety, provides additional details regarding conventional application of the algorithm. This algorithm works generally well when the source and target are initially close and when all of the points in the source have a corresponding point in the target. If, however, points exist in the source that are "far" from any true correspondence in the target, the minimization of the transform based on the chosen "false" correspondence can inhibit actual registration. In particular, when sensor data containing outliers is chosen to be the source, the outliers do not have true correspondences with the model and the registration fails. Similarly, when the sensor data does not completely cover the model, using the model as the source fails.

Accordingly, recognized by Applicants is the need for a system, program product, and methods to perform automated three-dimensional model registration, which allows both noisy and incomplete sensor data to be automatically registered without manual designation of the areas of correspondence and without ad hoc filtering of the data sources.

SUMMARY OF THE INVENTION

In view of the foregoing, embodiments of the present invention advantageously provide a system, program product, and methods to perform automated three-dimensional model registration, which allows both noisy and incomplete sensor data to be automatically registered without manual designation of the areas of correspondence and without ad hoc filtering of the data sources. Embodiments of the present invention also advantageously provide a system, program product, and methods to perform automated three-dimensional model registration, which allow noisy sensor data to be used, as it is, without modification, without identifying areas of interest and without an identification of initial point correspondences between the model and the range (sensor) data. Embodiments of the present invention also advantageously provide a system, program product, and methods which provide for acquisition of a model and a set of sensor data, positioning the model data close to the correct position with respect to the sensor data, and application of an algorithm on the model and sensor data whereby the final transformation represents the registration of the model to the sensor data. Embodiments of the present invention improve upon application of the "Iterative Closest Point" (ICP) algorithm by providing a mechanism to automatically reject outliers and bridge holes in noisy and incomplete sensor data, for example, using two applications of the ICP algorithm, e.g., swapping the source and target.

Specifically, embodiments of the present invention include a system to perform automated three-dimensional image registration for nondestructive evaluation of a part that is remotely positionable within an inspection cell. For example, according to an embodiment of the present invention, the system can include a laser-ultrasound inspection device having a scanning head including an ultrasonic source to generate ultrasonic surface displacements in a remotely positioned part positioned within a pre-defined inspection cell, an inspection laser, and an interferometer to collect phase modulated light reflected by the remotely positioned part during scanning by the inspection laser. The system can also include a part position locator, such as, for example, a structured light camera, positioned to measure a distance between a plurality of points on at least one surface of the remotely positioned part and a scanning laser reference location. The plurality of points collectively represent a measured pose of the at least one surface of the remotely positioned part when positioned within the inspection cell. The part position locator can include a scanning laser positioned to provide an optical source and having the reference location associated therewith, at least one scanning mirror positioned to direct the optical source along the at least one surface of the remotely positioned part, and an optical receiver position to receive reflected laser light provided by the scanning laser and reflected from the at least one surface of the part to thereby determine the distance between a plurality of points on the at least one surface of the part and the scanning laser reference location. The system can also include a database containing a plurality of computer-aided design models for each of a corresponding plurality of parts of interest, and at least one model of the inspection cell. The system can also include a laser ultrasound inspection computer communication with the laser-ultrasound inspection device and the part position locator, and having a processor and memory in communication with the processor storing laser ultrasound inspection program product adapted to perform automated three-dimensional image registration of the part.

Embodiments of the present invention also include program product stored in a tangible computer medium. For example, laser ultrasound inspection program product can be provided according to an embodiment of the present invention, which includes instructions that when executed by a computer, such as the laser ultrasound inspection computer, cause the computer to perform the operations of retrieving or otherwise receiving model data for a three-dimensional model of the part, retrieving or otherwise receiving data representing points on at least one surface of a part when in a measured pose within the inspection cell defining range data, aligning the three-dimensional model of the part to the measured pose of the part, associating gathered inspection data onto the three-dimensional model at the part pose to provide enhanced visualization of the inspection data, and mapping the inspection data into the model at the part pose responsive to registration of the part to the three-dimensional model of the part. The operation of aligning can include performing a registration of the three-dimensional model to the range data including identifying a set of points in the range data having a high probability of corresponding to actual points on the three-dimensional model, and performing a registration of the identified set of points in the range data having a high correspondence probability to the three-dimensional model. The operation of aligning can also include determining a composition of a first transformation between data points on the model of the part defining model data as a source and the range data as a target, and an inverse of a second transformation between the set of points in the range data having a high probability of corresponding to actual points on the model, to register the part with the three-dimensional model of the part.

The operation of performing a registration of the three-dimensional model to the range data can include utilizing data points on the model of the part defining model data as a source and the range data as a target, and determining the set of points in the range data having a high probability of corresponding to actual points on the model and a transformation "T1" therebetween. The set of points in the range data having a high probability of corresponding to actual points on the model can be a set of points in the range data that are closest to corresponding points in the model as calculated using an iterative closest point algorithm. The operation of performing a registration of the identified set of points in the range data having a high correspondence probability to the three-dimensional model can also include utilizing the identified set of points in the range data as a source and the model data as the target, and determining a transformation "T2" therebetween, and the operation of aligning can include determining a composition of the transformation T1 and an inverse of the transformation T2 to register the part with the three-dimensional model of the part. Advantageously, the registration of the part with the three-dimensional model of the part provides a robust match independent of both an existence of outliers in the range data and missing data in the range data. Further, advantageously, the operation of aligning the three-dimensional model of the part to the measured pose of the part within the inspection cell is performed without pre-filtering the range data to remove outliers or a pre-accounting for missing data.

Embodiments of the present invention also include methods of performing automated three-dimensional image registration of a part remotely positionable within an inspection cell. According to an embodiment of such a method, the method can include the steps of determining a location of a plurality of points on at least one surface of a part to be inspected when positioned within the inspection cell defining range data, identifying a set of points in the range data having a high probability of corresponding to data points on a three-dimensional model of the part to be inspected, determining a first transformation T1 between the data points on the three-dimensional model and the set of points in the range data having a high probability of corresponding to actual points on the model, such as, for example, to remove outliers, determining a second transformation T2 between the set of points in the range data having a high probability of corresponding to actual points on the model and the data points on the three-dimensional model, such as, for example, to account for missing data-removes bias if model covers more of the part than the range data. The steps can also include determining a composition of the first transformation with an inverse of the second transformation to thereby align the three-dimensional model with the part at part pose, and associating gathered inspection data onto the three-dimensional model at the part pose to provide enhanced visualization of the inspection data.

Embodiments of the present invention also include computer readable media that is readable by a computer to perform automated three-dimensional image registration of a part. According to an embodiment of the computer readable medium, the computer readable medium can include a set of instructions that, when executed by the computer, cause the computer to perform the operations of retrieving or otherwise receiving model data for a three-dimensional model of the part, retrieving or otherwise receiving data representing points on at least one surface of a part when in a measured pose within the inspection cell defining range data, aligning the three-dimensional model of the part to the measured pose of the part, associating gathered inspection data onto the three-dimensional model at the part pose to provide enhanced visualization of the inspection data, and mapping the inspection data into the model at the part pose responsive to registration of the part to the three-dimensional model of the part.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout.

Various systems such as non-destructive evaluation systems can use or employ a wide area, imaging device. Such systems also use, for example, a three-dimensional scanner to locate the part within a work cell. The three-dimensional scanner, for example, can create a point cloud of geometric samples ("point data") on the surface of the part. Such point data can represent the pose of a part in a given environment ("sensor data"). The point data is usually not directly utilized. Instead, various techniques including image registration techniques are used to define coordinate frames that allow the system to relate the three-dimensional data from the imaging device to a computer-aided design ("CAD") model of the part. The system can then map the sensor data from various viewpoints onto the CAD model, creating a three-dimensional coordinate frame for the operator to relate indications and evaluate scan coverage.

FIGS. 1-9 illustrate an exemplary laser-ultrasound based inspection system 30 for scanning, e.g., composite parts, which includes program product and improved methods of performing a three-dimensional alignment of a model to a measured pose of the part or parts, according to an embodiment of the present invention. As perhaps best shown in FIG. 1, the system 30 can include a laser-ultrasound inspection device 31, a part position locator 33, a laser ultrasound inspection computer 35, an area network 37, laser ultrasound inspection program product 39, computer aided design models ("CAD") 41 for each part of interest 43 stored in at least one database 45, and a model 47 of an inspection cell 49 stored in the at least one database 45, each described in more detail below.

Figure 1:
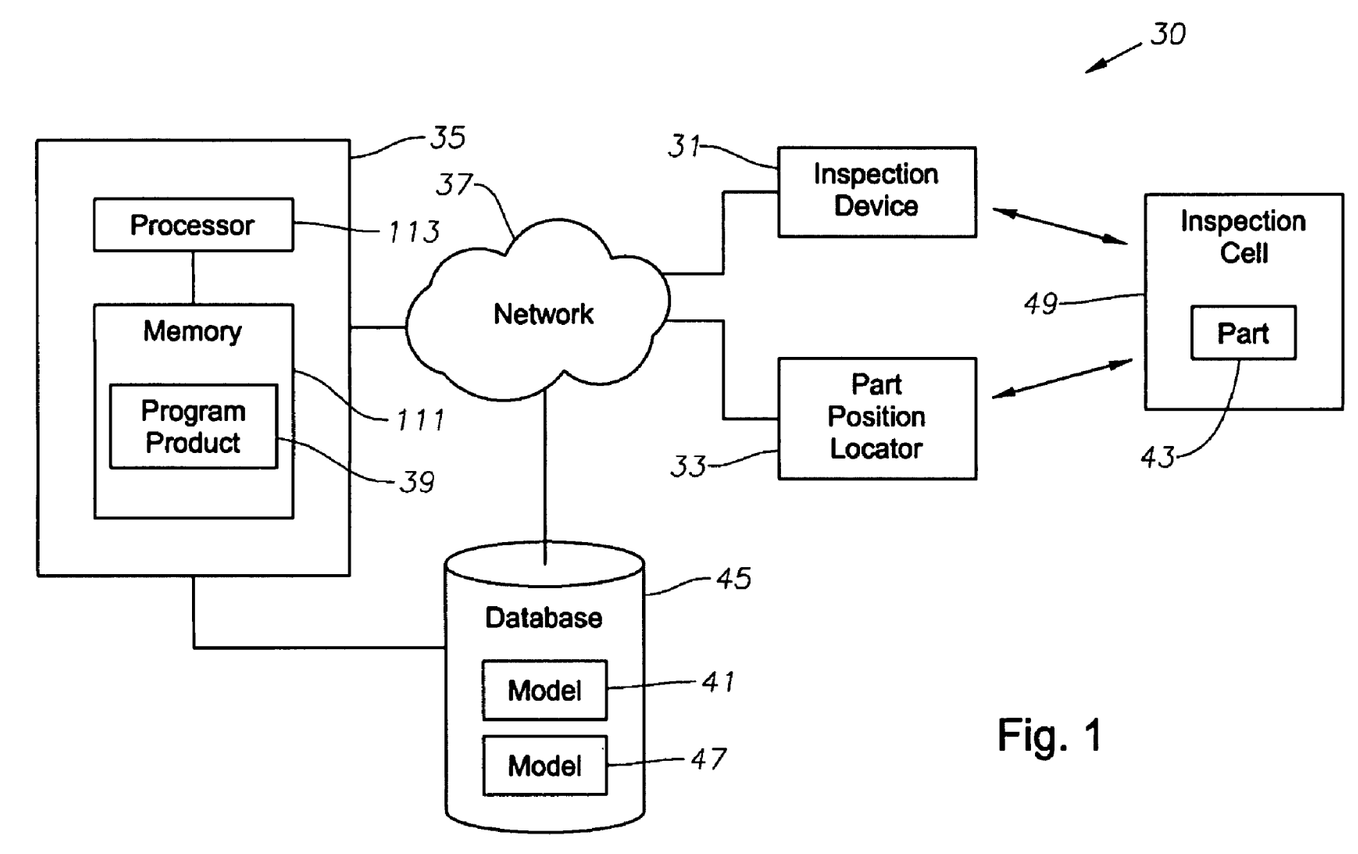
FIG. 1 is a schematic block diagram of a system to perform automated pre-dimensional image registration for nondestructive evaluation according to an embodiment of the present invention.
Figure 2A:
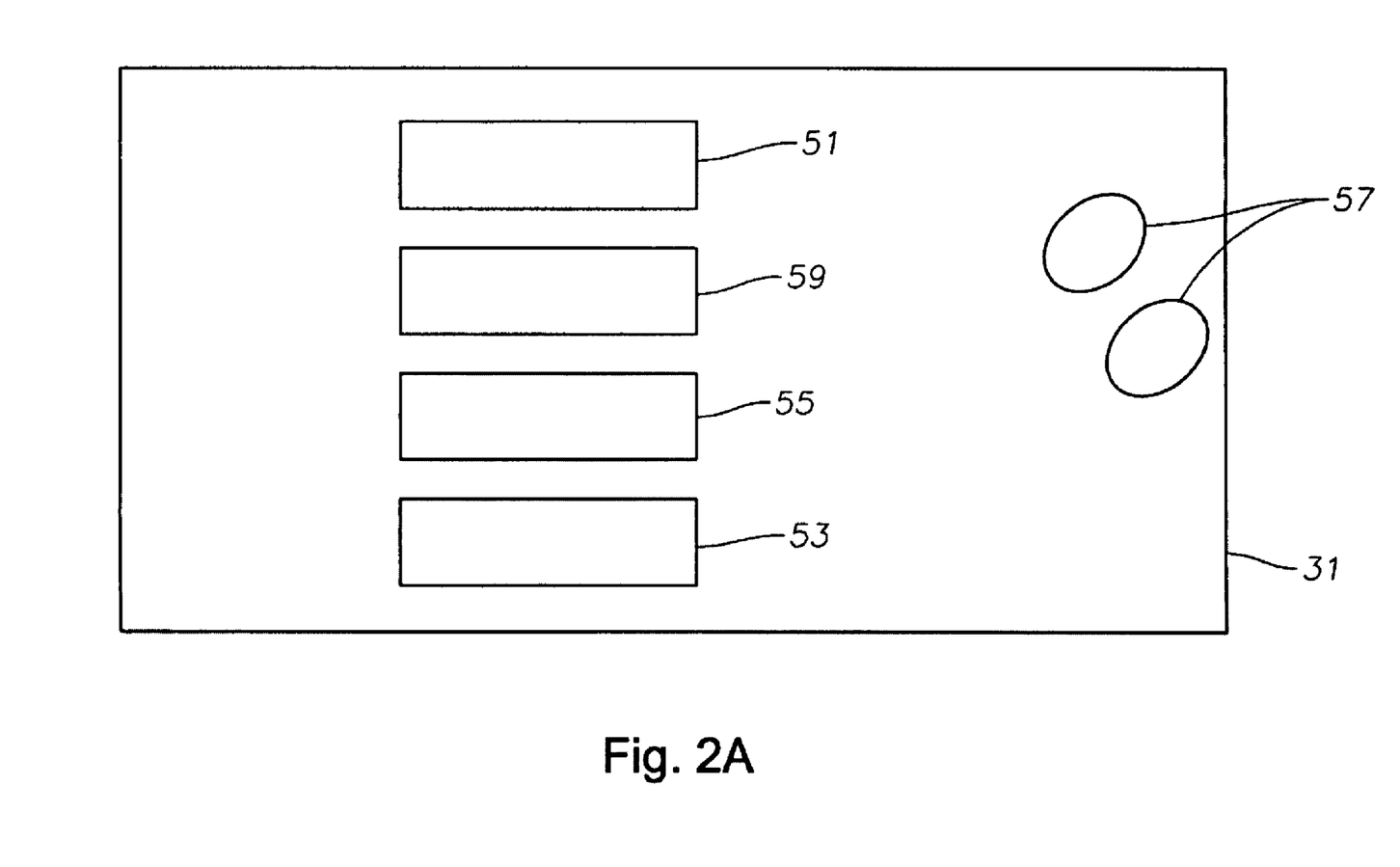
FIG. 2A is a schematic block diagram of a laser ultrasound inspection device according to an embodiment of the present invention.
Figure 2B:
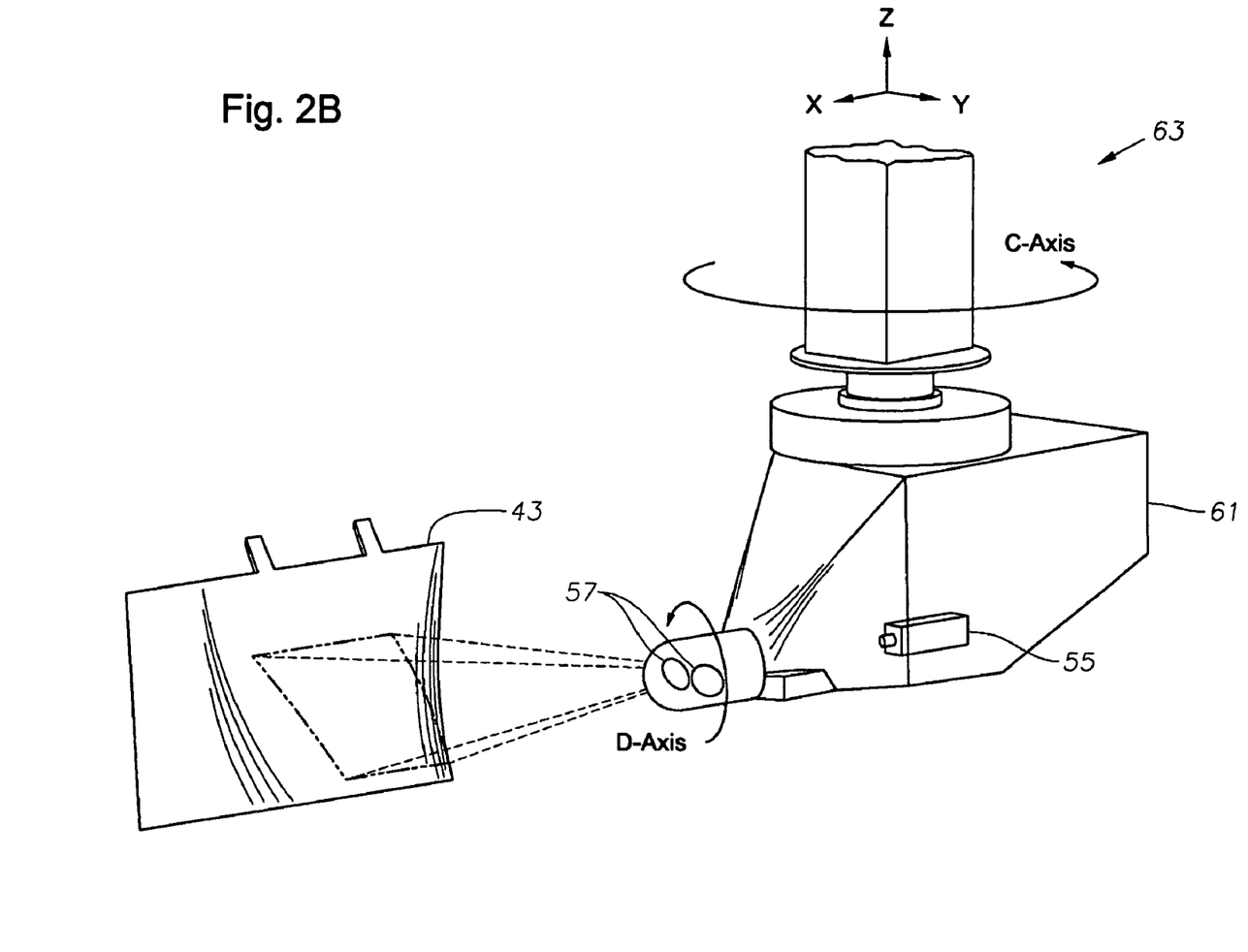
FIG. 2B is a perspective view of a laser ultrasound inspection device gantry or scanning head carried by a gantry according to an embodiment of the present invention.

As shown in FIG. 2A, the laser ultrasound optics of the laser ultrasound inspection device 31 can include a pointing laser 51 to indicate a scan position on the part 43, a heating laser or other ultrasound generating source 53, a scanning laser 55, at least one, but preferably at least two, scanning mirrors 57, and an interferometer or other optical receiver 59 to collect the phase modulated light reflected by the part during scanning, to thereby detect surface displacements. As shown in FIG. 2B, the various laser-ultrasound optics can be mounted, for example, in a gantry or scanning head 61 having, e.g., five degrees of freedom. Such configuration can allow the optics to be positioned in X, Y, and Z, and rotated around a vertical axis C and horizontal axis D. In operation, the gantry head 61 can be moved so that the scanning laser 55 is positioned, for example, approximately sixty inches from the part 40 and is approximately perpendicular to the surface. According to such specific configuration, the scanning technique is effective at up to, for example, approximately ±60 degrees from perpendicular. According to one preferred configuration applicable to larger parts, a single scan can therefore cover up to a six by six square foot section of the part by moving two scanning mirrors contained within the scanning head. Of course, different configurations and different mirror positioning can provide different scanning capability.

According to the above described configuration, no head movement is required during the scan, but multiple gantry positions may be utilized to completely inspect a given part, for example, due to occlusion, extent, and surface normality constraints. The output of each scanning (inspection) operation includes a two-dimensional (2D) ultrasonic image depicting the inspection data for the portion of the part 43 covered by the scan. The union of all the images produced represents the complete inspection data acquired on the part 43 (see FIG. 9). Spacing on the ultrasonic images can be controlled such that each pixel represents a constant spacing on a canonical plane placed perpendicular to the laser source and at a fixed distance from the scanning head.

A benefit of this configuration over more traditional inspection technology is the ease of scan set up and retooling. The system 30 can generate usable data over wide angles of incidence of the scanning laser 55 to the part surface and can tolerate minor variations in the positioning of the part 43 from one scan to the next. This allows the part 43 to be staged in the inspection cell 49 (FIG. 1) using "soft" tooling. Such soft tooling can include an inspection table (not shown) with pre-positioned holes into which a series of pegs and posts can be inserted, primarily to provide visual cues as to when the part is correctly positioned, without the need for expensive fixtures or significant modifications.

It is useful to localize the ultrasonic data to an actual position on, for example, a CAD model. Beneficially, such localization can allow defects and part features discovered during the inspection process to be brought back into the model for analysis. Subsequently, stress and strain calculations can be used to predict part performance and likelihood of failure. Further, defects can be put into context so that they can be compared across parts, or compared versus as built/in-service. Still further, over- and under-coverage can be readily determined.

Figure 3A:
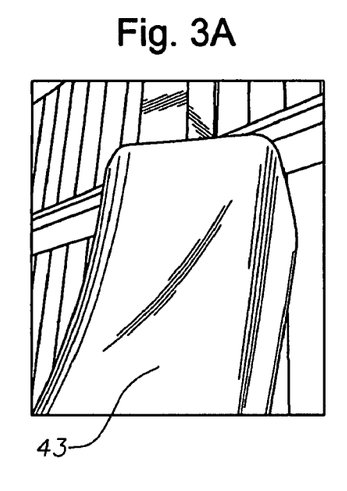
FIGS. 3A-C are a sequence of perspective views of a part to be inspected according to an embodiment of the present invention.
Figure 3B:
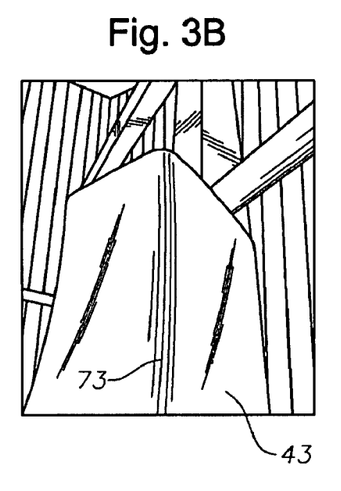
Figure 3C:
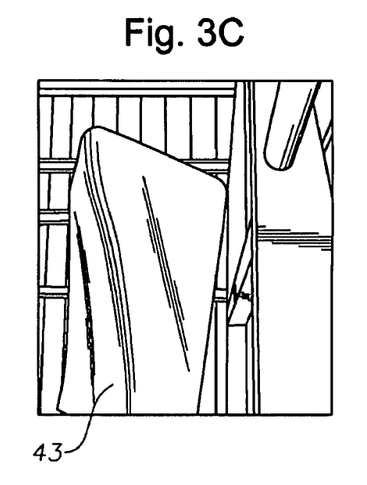
Figure 4A:
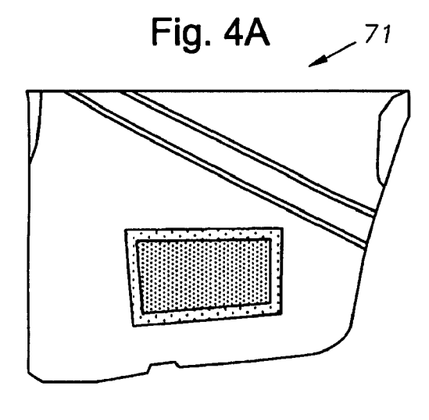
FIGS. 4A-C are a sequence of two-dimensional ultrasonic images generated by a scanning process with the part in the positions shown in FIGS. 3A-C according to an embodiment of the present invention.
Figure 4B:
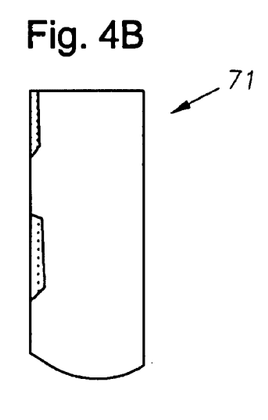
Figure 4C:
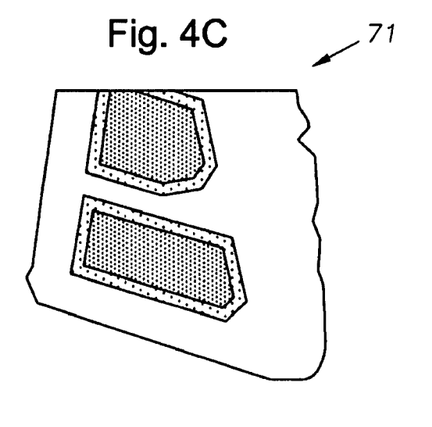

Conventionally, an inspector is presented with ultrasonic images and determines from those images the status of a part 43 and the location of any defects. FIGS. 3A-C show a sequence of three views of a part 43 within the inspection cell 49. FIGS. 4A-C show a sequence of ultrasonic (data) images 71 generated by the scanning process with the part 43 in the positions shown in FIGS. 3A-C. Looking at the ultrasonic image data, it is difficult to ascertain the actual coverage of the part 43 within the scanned region. Note, the darker color segments shown in FIGS. 4A-C indicate areas where the structure is thinner than others. Note also, the images shown in FIGS. 4A-C are oriented 180 degrees from vertical, as typically delivered.

The images shown in FIGS. 3A and 3B appear to cover a seam 73, but the quality of the data in the overlap region is not well defined. It is possible that the image shown in FIG. 3B is unnecessary (over-scan), but it is equally possible that the seam is incompletely covered (under-scan) when only the images shown in FIGS. 3A and 3B are used. Similarly, accurate defect positions are important for determining interactions among near defects, for analyzing growth and stress characteristics using modeling analyses, for maintaining archives of frequent defect locations, and for matching as-built data to in-service data. These analyses can become more complex when coupled with soft tooling, as known to those skilled in the art, which may shift the relative position of images from scan to scan.

In order to improve the presentation of data to the inspector and to improve the localization of defects, the system 30 can capture the effects of the soft tooling on the pose of the part 43 within the scan/inspection cell 49 and can use computer visualization techniques to reapply the ultrasonic data back onto the corrected version of an underlying CAD model. This improved presentation can reduce or eliminate many of the issues of the current presentation, allowing defect locations to be determined precisely for modeling and analysis, and allowing scan coverage to be precisely determined and measured for a specific part pose. Beneficially, the presentation of the ultrasonic data can be decoupled from the scan parameters and be presented to the inspector in a natural and more efficient way. As an additional benefit, these same techniques can be used as the basis of a scan planning application designed to automatically determine a set of scans that provide full coverage while minimizing over-scan. The method, according to an embodiment of the present invention, includes four steps: (1) model the gantry kinematics and inspection cell features, (2) measure the location of the part in the inspection cell (defining the pose of the scanned part), (3) align the CAD model to the pose, and (4) map the ultrasound data onto the repositioned CAD model.

Modeling the Gantry and Inspection Cell.

Figure 5:
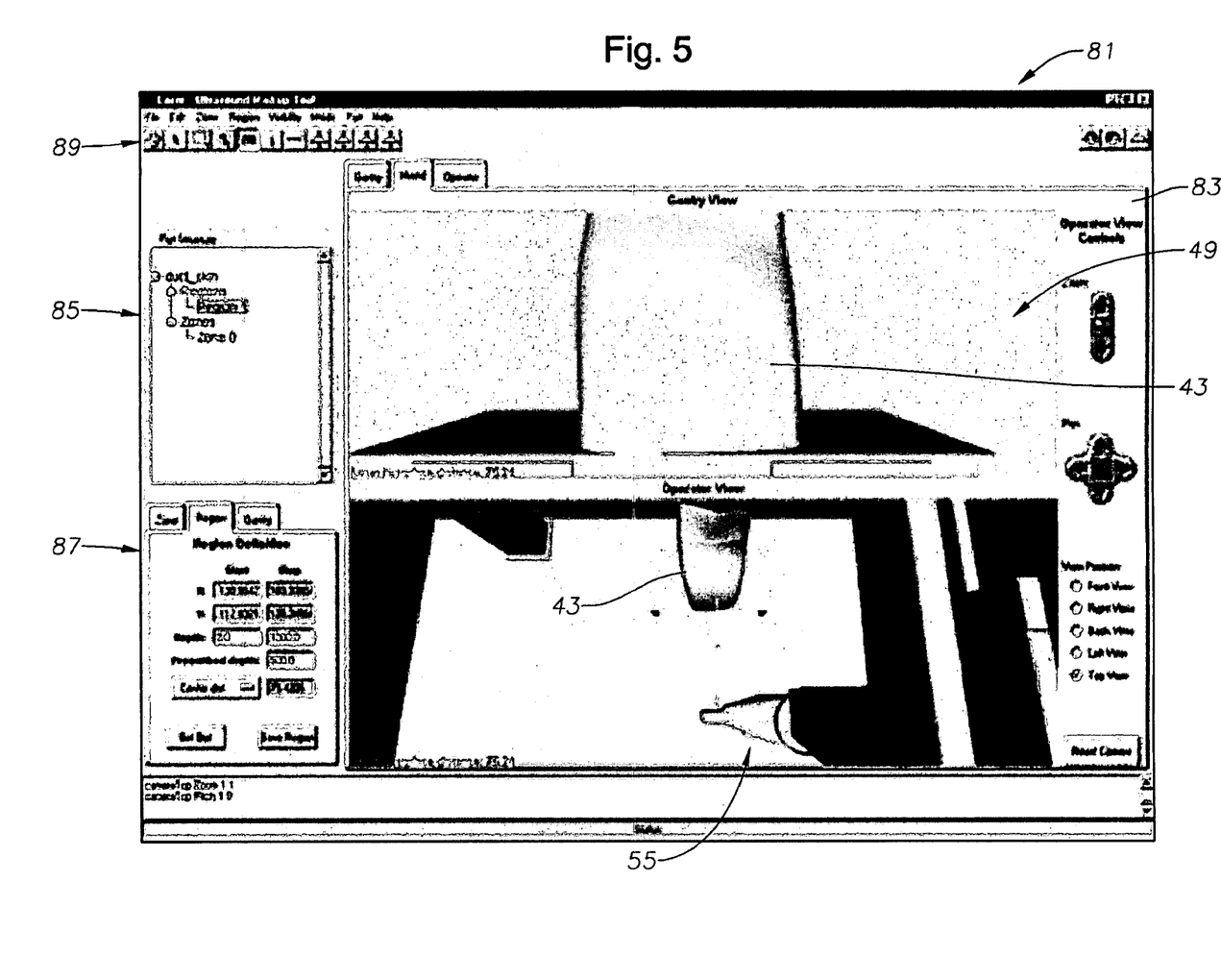
FIG. 5 is a screen shot of a graphical user interface presenting a display frame showing two views into an inspection cell according to an embodiment of the present invention.

As noted above, the models database 41 can include a complete model 47 of the scan/inspection cell 49 within which a model of the gantry 63 can be accurately modeled, animated, and positioned. This beneficially can allow a CAD model of a part 43 to be placed within the scan/inspection cell 49; can allow existing scan plans to be simulated, displayed, and analyzed using a model of the existing hardware interface; and can allow one-touch positioning of the gantry head 61 to defined scan positions. This virtual environment can beneficially allow the operator to simulate operations on model data and to carry out much of the required preprocessing work without the need for access to the scan/inspection cell 49. The virtual environment can provide part positioning, scan analysis, and visualization and can form the basis for both automated scan planning and improved visualization efforts. FIG. 5 shows a screen shot of a graphical user interface 81 presenting a display frame 83 showing two views into an inspection cell 49. The upper panel depicts the cell 49 as seen from the scanning laser 55 while the lower panel depicts the view from one of five defined positions in the cell 49. Field section 85 provides gantry positions and field section 87 provides gantry position control tabs. The graphical user interface 81 also can include various selections in the menu bar 89 and those shown positioned around the frame 83 allow the simulation to be controlled and modified. Other windows displayable in the displayed field of the graphical user interface 81 can show areas of the part 43 where scan constraints (angle of incidence, distance, and etc.) are met, provide for part positioning, and allow other operations useful to a virtual scan operation.

Measuring the Position of the Part in the Inspection Cell.

As noted above, soft tooling can be used during the scanning process to improve the usability of the system 30, decrease the cost of new part development, and increase throughput. A user of the system 30 can stage all of the scanned parts 43 on a single optical table (not shown) having, for example, pegs and posts to provide visual cues for correct alignment. According to such implementation, no new fixturing hardware needs to be provided in order to scan additional parts 43. Staging a new part 43 using the optical table can be as simple as choosing a set of holes that provide a "replicable" part pose. Unfortunately, this methodology does not generally provide for true replication of part position or pose from scan to scan and from part to part. As such, any attempt to accurately position the ultrasonic images 71 on the CAD model requires determining the position and pose of the part 43 and requires repositioning the CAD model of the part 43 for each individual set of scan (inspection) data. According to an embodiment of the system 30, to accomplish this, the laser ultrasound gantry 63 can be augmented with a part position locator 33 such as, for example, a structured light range camera, e.g., the Structure Light (SL) Vision camera, developed at Sandia National Laboratories.

Figure 6:
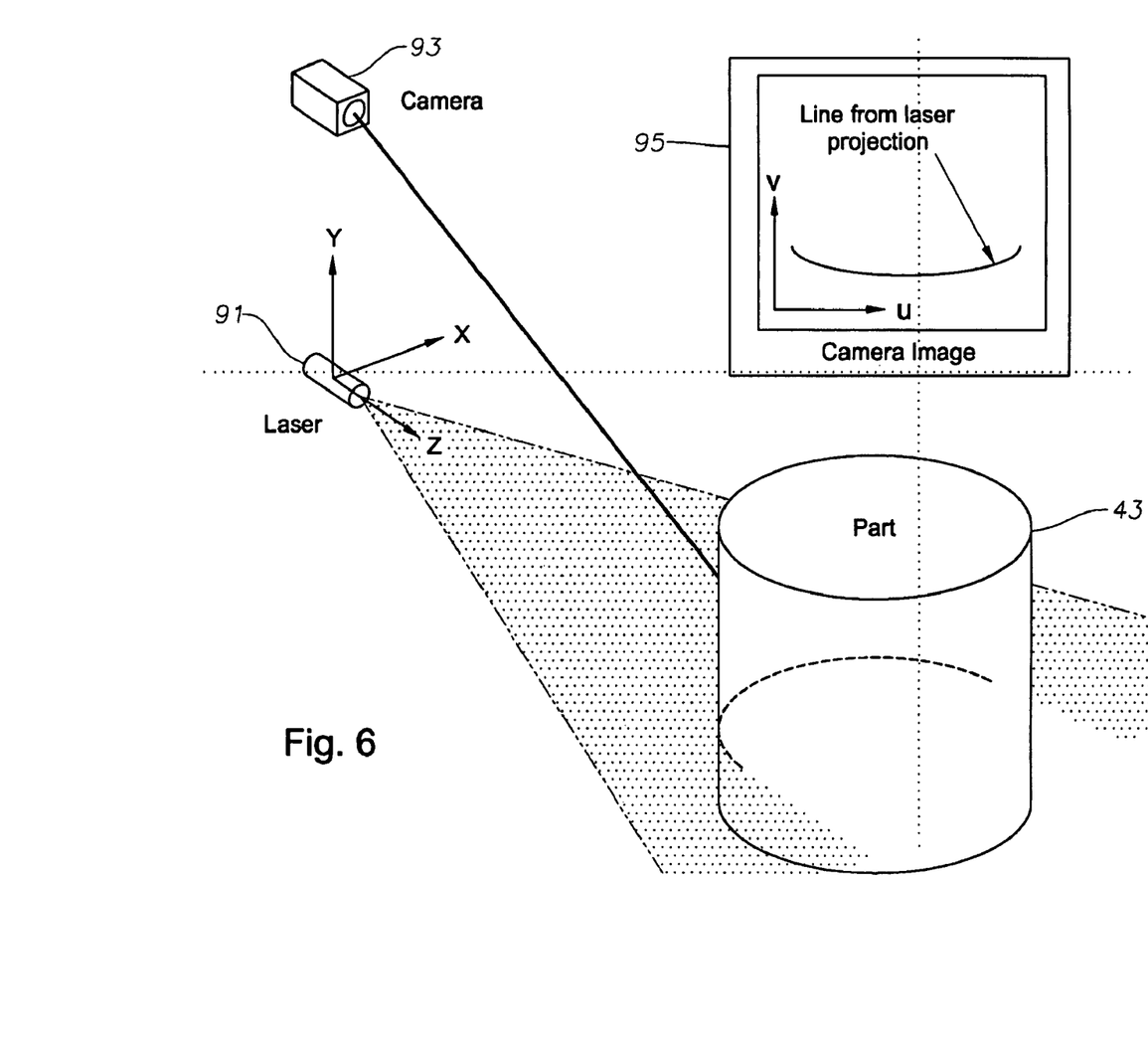
FIG. 6 is an environmental view of a part position locator in operation according to an embodiment of the present invention.
Figure 7:
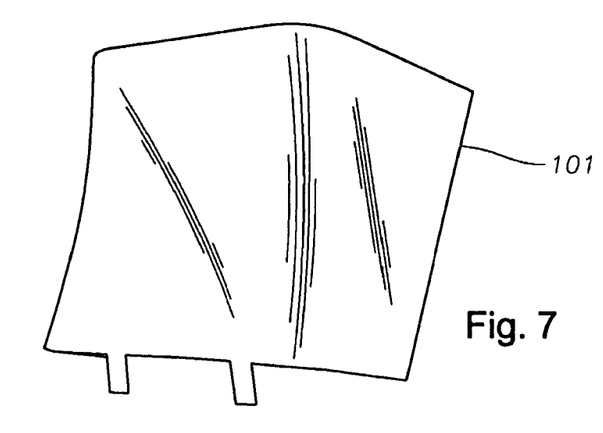
FIG. 7 is a perspective view of a three-dimensional model of a part to according to an embodiment of the present invention.

As perhaps best illustrated in FIG. 6, in a preferred configuration, the part position locator 33 includes a range laser 91 in the form of a laser striper, and a notch-filtered camera 93 to determine the distance of the part 43 to the scanning laser 55. Note, as perhaps best shown in pixel graph 95, in this configuration, due to the notch filter, the camera 93 substantially only sees the intensity of the stripe (line) projected by the laser striper 91 on the part 43. This information is combined with knowledge of the position of the scanning laser 55 at the collection point to provide a cloud of points at the part position. This collection can take place at a number of different gantry positions that provide a set of data that together represent the part 43 in the cell 49 at the part pose. According to one embodiment of the system 30, the part position locator 33 includes memory and independent software to collect the cloud of points. According to another embodiment of the system 30, the part position locator 33 interfaces directly with and/or is controlled by the laser inspection computer 35 via the laser ultrasound inspection program product 39.

Accuracy of the data is important. As such, the range laser 91 and camera 93 can be calibrated to remove intrinsic distortions such as lens effects, misalignment of the camera image plane, and other camera intrinsics, as well as to determine the pose of the camera and laser, both relative to one another, and relative to the laser ultrasound gantry 63. According to an embodiment of the system 30, a calibration procedure can be utilized which, for example, can point the part position locator 33 at different points in a scene by changing the pan and tilt settings of the camera 93, or by moving the gantry head 61, and then finding correspondences between the camera image and fixed known positions in the physical world (e.g., associate or otherwise transform the coordinate system of the part position locator 33 to the coordinate system of the inspection cell 49). A two-stage calibration procedure can be utilized which first calibrates the intrinsics of the part position locator 33 and pose of the part position locator components with respect to one another, for example, using a texture camera (not shown); and second determines target centers using image-processing techniques to calibrate/determine the pose of the texture camera with respect to the scanning laser 55 to thereby determine three-dimensional distances to the camera 93 to give the three-dimensional points along the surface of the part 43. Such methodology is generally described, for example, in Turner et al., "Using Computer Vision to Map Laser Ultrasound onto CAD Geometries," Review of Quantitative Nondestructive Evaluation, 22, American Institute of Physics (2003), incorporated by reference herein in its entirety.

Aligning the CAD Model to the Pose of the Part.

Figure 8:
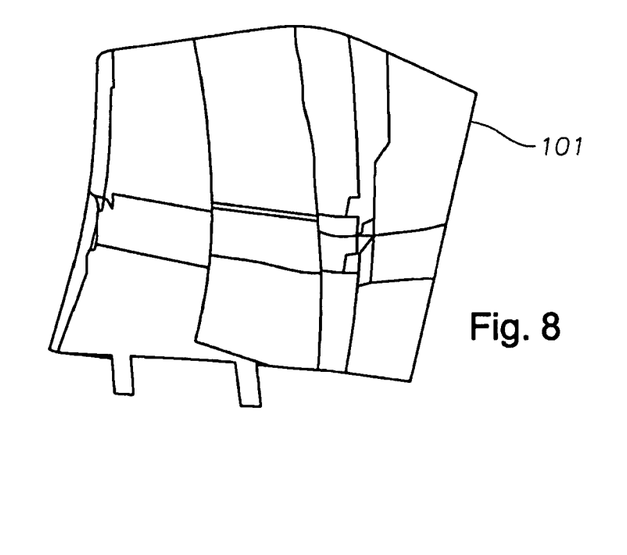
FIG. 8 is perspective view of the model shown in FIG. 7 combined with range data to illustrate a registration including multiple non-overlapping range data segments generated by a multi-view scan of a part according to an embodiment of the present invention.

At this point in the process, the system 30 has access to: an accurate model 47 of the inspection cell 49 with the ability to animate gantry motion; an accurate specific CAD model 101 of the part 43 (FIG. 7) of the plurality of models 41 stored in database 45; and a point cloud of data (determined above) representing points on the part 43 in its true pose within the inspection cell 49. The next step is to move the CAD model 101 so that it correctly matches the point data collected, referred to as registration. The ultimate results of such registration is illustrated in FIG. 8 which shows multiple (e.g., fifty-seven) non-overlapping segments generated by a more complete eleven-view scan of the part 43. This step/operation (series of steps/operations) is complicated by the nature of the collected range data which may include points corresponding to other surfaces in the inspection cell 49 for such as the table upon which the part 43 is staged, walls of the scanning/inspection cell 49, (collectively outliers); data which may not completely cover the part 43 to be scanned because of occlusion, or field of view limitations (collectively missing data); and system noise (i.e., errors in statistical accuracy of the range data); etc.

Beneficially, the laser ultrasound inspection program product 39 stored in the memory 111 of the laser ultrasound inspection computer 35 can include instructions that when executed by the processor 113 of the computer 35, cause the computer 35 to implement operations to perform the alignment of the model of the respective part 43 to the collected part data in its measured pose. Note, the memory 111 can include volatile and nonvolatile memory known to those skilled in the art including, for example, RAM, ROM, and magnetic or optical disks, just to name a few. The program product 39 can be in the form of microcode, programs, routines, and symbolic languages that provide a specific set for sets of ordered operations that control the functioning of the hardware and direct its operation, as known and understood by those skilled in the art. Note also, the program product 39, according to an embodiment of the present invention, need not reside in its entirety in volatile memory, but can be selectively loaded, as necessary, according to various methodologies as known and understood by those skilled in the art.

According to an embodiment of the system 30, program product 39, and methods, the operator first loads the CAD model 101 and range data (e.g., point cloud of data) taken for the part 43 to be inspected into a part placement graphical user interface of the laser ultrasound inspection program product 39. According to another embodiment of the system 30, program product 39, and methods, the operator selects the CAD model 101 for the part 43 from the plurality of models 41 stored in the database 45, and if not automatically received, selects the range data to be used. Correspondingly, the laser ultrasound inspection program product 39 receives the three-dimensional model 101 of the part 43, and receives the point cloud of data. The operator, using an input device (e.g., mouse, trackball, touchscreen, etc.), then manually graphically moves the part 43 "close" to correspondence with the model 101. This initial alignment can be very rough yet still help ensure that the initial iteration of the registration process has a reasonable starting point. After this initial alignment, the part placement portion of the laser ultrasound inspection program product 39 is run against the point cloud and CAD model 101 without further operator interaction. Beneficially, as perhaps best shown in FIG. 8, this registration generates a robust fine match independent of the existence of outliers and with missing data in the point cloud representing the part.

According to an embodiment of the laser ultrasound inspection program product 39, in order to perform such registration process, the laser ultrasound inspection program product 39 includes instructions that when executed by the laser ultrasound inspection computer 35 causes the computer 35 to perform the operations of executing an iterative closest point algorithm with the model 101 as the source and the cloud of data (range sensor data) as the target. The output of this phase is a transformation "T1" and a set of points from the sensor data "S1." This set of points are the correspondences generated to the source points, i.e., they are a set of points in the range sensor data that are closest to points in the model 101 as calculated by the iterative closest point algorithm. The operations next include executing the iterative closest point algorithm again, this time using the set "S1" of points from the range sensor data as the source and the model data as the target. The output from this phase is a transform "T2." The operations next include determining the composition of the transformation T1 with the inverse of transformation T2 which defines the registration. According to this embodiment of the program product 39, the initial pass of the iterative closest point algorithm both provides a rough registration of the model 101 to range sensor data, and identifies a set of points in the range sensor data that have high probability of corresponding to actual points on the model 101. The second pass registers the identified high probability points to the model 101. The transform resulting from the above operations is the composition of the transform identified by the first pass with the inverse of the transform identified by the second pass.

Mapping the Ultrasound Data onto the Repositioned CAD Model.

Figure 9:
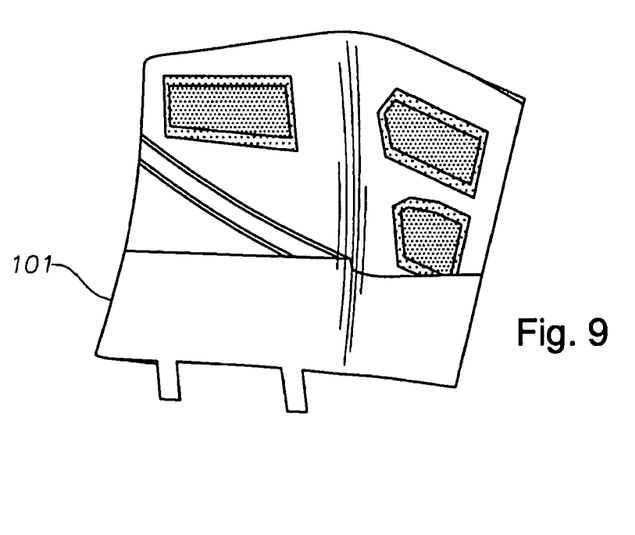
FIG. 9 is a perspective view of the registration shown in FIG. 8 having inspection data "wallpapered" onto the surface of the registered model according to an embodiment of the present invention.

As perhaps best shown in FIG. 9, according to an embodiment of the laser ultrasonic inspection program product 39, the operations further include mapping/remapping the gathered ultrasonic sensor data, such as, for example, that shown in FIGS. 4A-C, into the model 101 at the part pose to complete the association of the ultrasonic sensor data with the CAD model 101. This can be accomplished, for example, by projecting the ultrasonic data onto the part as a texture using visualization tools (not shown). The operations include generating a new instance of the model in the scene for every ultrasonic image the user desires to place on the CAD model 101. Turner et al. generally describes exemplary methodologies of performing such operations.

It is important to note that while embodiments of the present invention have been described in the context of a fully functional system, those skilled in the art will appreciate that the mechanism of at least portions of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include but are not limited to: nonvolatile, hard-coded type media such as read only memories (ROMs), CD-ROMs, and DVD-ROMs, or erasable, electrically programmable read only memories (EEPROMs), recordable type media such as floppy disks, hard disk drives, CD-R/RWs, DVD-RAMs, DVD-R/RWs, DVD+R/RWs, flash drives, and other newer types of memories, and transmission type media such as digital and analog communication links. For example, such media can include both operating instructions and operations instructions related to the laser ultrasound inspection program product 39 and the method steps, described above.

Embodiments of the present invention include several advantages. For example, embodiments of the present invention are sufficiently robust to allow registration of sensor (range) data to a model using noisy sensor data, as is, without modification, e.g., without ad hoc filtering; without identifying areas of interest; and without designation of areas of correspondence, i.e., manual identification of initial point correspondences between the model and range data. Embodiments of the present invention employ an algorithm which is automatically run on the model and sensor data and which produces a final transform representing the registration of the model to the sensor data. Embodiments of the present invention perform such automated registration requiring little more than acquisition of a model and a set of sensor data, and initial manual graphical positioning of the model data close to the correct position with respect to the sensor data, or vice versa. Embodiments of the present invention perform the automatic registration by employing a variant of the iterative closest point algorithm which provides two passes of the iterative closest point algorithm, swapping the source and the target on the second pass, and thereby help negate the effects of noisy or incomplete sensor data.

This application is related to U.S. Provisional Patent Application No. 61/040,415, filed Mar. 28, 2008, titled "System, Program Product, and Related Methods for Registering Three-Dimensional Models to Point Data Representing the Pose of a Part," incorporated herein by reference in its entirety.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. For example, techniques employed according to various embodiments of the present invention can be used for a variety of nondestructive evaluation, shape inspection, and general navigation/manipulation applications, which utilize laser, non-laser, or both methodologies to generate inspection data. Accordingly, those skilled in the art will recognize applicability of the various embodiments of the present invention to a variety of applications.

The invention claimed is:

1. A system to perform automated three-dimensional image registration for nondestructive evaluation of a part remotely positionable within an inspection cell, the system comprising:
  a laser-ultrasound inspection device having a scanning head including:
    an ultrasonic source to generate ultrasonic surface displacements in a remotely positioned part positioned within a pre-defined inspection cell,
    an inspection laser, and
    an interferometer to collect phase modulated light reflected by the remotely positioned part during scanning by the inspection laser, the phase-modulated light modulated by the ultrasonic surface displacements in the remotely positioned part to provide inspection data;

a part position locator positioned to measure a distance between a plurality of points on at least one surface of the remotely positioned part and a scanning laser reference location, the plurality of points collectively representing a measured pose of the at least one surface of the remotely positioned part when positioned within the inspection cell, the part position locator including:
- a scanning laser positioned to provide an optical source and having the reference location associated therewith,
- at least one scanning mirror positioned to direct the optical source along the at least one surface of the remotely positioned part, and
- an optical receiver positioned to receive reflected laser light provided by the scanning laser and reflected from the at least one surface of the part to thereby determine the distance between a plurality of points on the at least one surface of the part and the scanning laser reference location;

a laser ultrasound inspection computer in communication with the laser-ultrasound inspection device and the part position locator, and including a processor and memory in communication with the processor; and laser ultrasound inspection program product stored in the memory of the laser ultrasound inspection computer and including instructions, that when executed by the processor of the laser ultrasound inspection computer, cause the computer to perform the operations of:
- receiving model data for a three-dimensional model of the remotely positioned part,
- receiving from the part position locator a point cloud of data representing points on the at least one surface of the remotely positioned part when in the measured pose within the inspection cell defining range data, and
- aligning the three-dimensional model of the remotely positioned part to the measured pose of the part within the inspection cell, the operation of aligning including:
  - performing a registration of the three-dimensional model to the range data to include utilizing data points on the three-dimensional model of the remotely positioned part as a source and the range data as a target and identifying a set of points in the range data having a high probability of corresponding to actual points on the three-dimensional model, and
  - performing a registration of the identified set of points in the range data having a high correspondence probability to the three-dimensional model, to include utilizing the range data having a high probability of corresponding to actual points on the three-dimensional model as a source and data points on the three-dimensional model of the remotely positioned part as a target.

2. The system as defined in claim 1,
wherein the operations further include the operation of associating gathered inspection data onto the three-dimensional model at the part pose to provide enhanced visualization of the inspection data; and
wherein the system further comprises a database containing a plurality of computer-aided design models for each of a corresponding plurality of parts of interest, and at least one model of the inspection cell.

3. The system as defined in claim 1, wherein the operation of performing a registration of the three-dimensional model to the range data includes:

determining a transformation between data points on the three-dimensional model and the set of points in the range data having a high probability of corresponding to actual points on the three-dimensional model of the part.

4. The system as defined in claim 3,
wherein the transformation is a first transformation T1; and
wherein the set of points in the range data having a high probability of corresponding to actual points on the three-dimensional model includes a set of points in the range data that are closest to corresponding points in the three-dimensional model as calculated using an iterative closest point algorithm.

5. The system as defined in claim 3, wherein the transformation is a first transformation T1, and wherein the operation of performing a registration of the identified set of points in the range data having a high correspondence probability to the three-dimensional model includes:
determining a second transformation T2 between the set of points in the range data having a high probability of corresponding to actual points on the three-dimensional model of the part and data points on the three-dimensional model.

6. The system as defined in claim 5, wherein the operation of aligning includes determining a composition of the first transformation T1 and an inverse of the second transformation T2 to register the remotely positioned part with the three-dimensional model of the part.

7. The system as defined in claim 6, wherein the registration of the remotely positioned part with the three-dimensional model of the part provides a robust match independent of both an existence of outliers in the range data and missing data in the range data.

8. The system as defined in claim 6, wherein the operations further comprise mapping the inspection data into the three-dimensional model of the part at the part pose responsive to registration of the remotely positioned part to the three-dimensional model of the part.

9. The system as defined in claim 6, wherein the operation of aligning the three-dimensional model of the remotely positioned part to the measured pose of the part within the inspection cell is performed without pre-filtering the range data to remove outliers or a pre-accounting for missing data.

10. The system as defined in claim 6, wherein the laser-ultrasound inspection device and the part position locator are mounted in a scanning head having five degrees of freedom.

11. Program product to perform automated three-dimensional image registration of a part comprising instructions stored in a non-transitory computer readable medium that when executed by a computer, cause the computer to perform the operations of:
- receiving model data for a three-dimensional model of a part;
- receiving data representing points on at least one surface of the part when in a measured pose within an inspection cell defining range data; and
- aligning the three-dimensional model of the part to the measured pose of the part, the operation of aligning including:
  - performing a registration of the three-dimensional model to the range data to include utilizing data points on the three-dimensional model of the part as a source and the range data as a target and determining a set of points in the range data having a high probability of corresponding to actual points on the three-dimensional model, and
  - performing a registration of the identified set of points in the range data having a high correspondence probability to the three-dimensional model, to include utilizing the range data having a high probability of corresponding to actual points on the three-dimensional model as a source and data points on the three-dimensional model of the part as a target.

12. The program product as defined in claim 11,
wherein the operation of performing a registration of the three-dimensional model to the range data further includes determining a composition of a first transformation T1 between data points on the three-dimensional model of the part and the range data, and an inverse of a second transformation T2 between the set of points in the range data having a high probability of corresponding to actual points on the three-dimensional model and data points on the three-dimensional model, to register the part with the three-dimensional model of the part; and
wherein the operations further include the operation of associating gathered inspection data onto the three-dimensional model at the part pose to provide enhanced visualization of the inspection data.

13. The program product as defined in claim 11, wherein the set of points in the range data having a high probability of corresponding to actual points on the three-dimensional model are a set of points in the range data that are closest to corresponding points in the three-dimensional model as calculated using an iterative closest point algorithm.

14. The program product as defined in claim 13,
wherein the transformation is a first transformation T1;
wherein the operation of performing a registration of the identified set of points in the range data having a high correspondence probability to the three-dimensional model includes determining a second transformation T2 between the set of points in the range data having a high probability of corresponding to actual points on the three-dimensional model of the part and data points on the three-dimensional model;
wherein the operation of aligning further includes determining a composition of the first transformation T1 and an inverse of the second transformation T2 to register the part with the three-dimensional model of the part; and
wherein the operations further comprise mapping the inspection data into the three-dimensional model at the part pose responsive to registration of the part to the three-dimensional model of the part.

15. The program product as defined in claim 14,
wherein the registration of the part with the three-dimensional model of the part provides a robust match independent of both an existence of outliers in the range data and missing data in the range data; and
wherein the operation of aligning the three-dimensional model of the part to the measured pose of the part within the inspection cell is performed without pre-filtering the range data to remove outliers or a pre-accounting for missing data.

16. A method of performing automated three-dimensional image registration of a part remotely positionable within an inspection cell, the method comprising the steps of:
determining by a computer, a location of a plurality of points on at least one surface of a part to be inspected when positioned within the inspection cell defining range data;
identifying by the computer, a set of points in the range data having a high probability of corresponding to data points on a virtual three-dimensional model of the part to be inspected;
determining by the computer, a first transformation T1 between the data points on the three-dimensional model and the set of points in the range data having a high probability of corresponding to actual points on the three-dimensional model;
determining by the computer, a second transformation T2 between the set of points in the range data having a high probability of corresponding to actual points on the three-dimensional model and the data points on the three-dimensional model;
determining by the computer, a composition of the first transformation T1 with an inverse of the second transformation T2 to thereby align the three-dimensional model with the part at part pose; and
associating by the computer, gathered inspection data onto the three-dimensional model at the part pose to provide enhanced visualization of the inspection data.

17. The method as defined in claim 16, wherein the step of identifying a set of points in the range data having a high probability of corresponding to data points on a three-dimensional model of the part to be inspected includes the step of determining a set of points in the range data that are closest to corresponding points in the three-dimensional model as calculated using an iterative closest point algorithm.

18. The method as defined in claim 16, wherein the aligning provides a robust match independent of both an existence of outliers in the range data and missing data in the range data.

19. The method as defined in claim 16, wherein the steps of determining a first transformation T1, a second transformation T2, and a composition of the first transformation T1 and inverse of the second transformation T2 are performed without pre-filtering the range data to remove outliers or a pre-accounting for missing data, without identifying a set of points on the part to manually register, and without manually selecting specific points in the three-dimensional model having correspondence with specific points in the data.

20. A method of performing automated three-dimensional image registration of a part remotely positionable within an inspection cell, the method comprising the steps of:
receiving by a processor model data for a virtual three-dimensional model of the part;
receiving by the processor data representing points on at least one surface of a part when in a measured pose within the inspection cell defining range data; and
aligning by the processor, the three-dimensional model of the part to the measured pose of the part, the step of aligning including:
performing a registration of the three-dimensional model to the range data to include utilizing data points on the three-dimensional model of the remotely positioned part as a source and the range data as a target and identifying a set of points in the range data having a high probability of corresponding to actual points on the three-dimensional model, and
performing a registration of the identified set of points in the range data having a high correspondence probability to the three-dimensional model, to include utilizing the range data having a high probability of corresponding to actual points on the three-dimensional model as a source and data points on the three-dimensional model of the part as a target.

21. A non-transitory computer readable medium to perform automated three-dimensional image registration of a part, the computer readable medium comprising a set of instructions that, when executed by a computer, cause the computer to perform the following operations:

receiving model data for a three-dimensional model of the part;

receiving data representing points on at least one surface of a part when in a measured pose within an inspection cell defining range data; and aligning the three-dimensional model of the part to the measured pose of the part, the operation of aligning including:

performing a registration of the three-dimensional model to the range data to include utilizing data points on the three-dimensional model of the remotely positioned part as a source and the range data as a target and determining a set of points in the range data having a high probability of corresponding to actual points on the three-dimensional model, and performing a registration of the identified set of points in the range data having a high correspondence probability to the three-dimensional model, to include utilizing the range data having a high probability of corresponding to actual points on the three-dimensional model as a source and data points on the three-dimensional model of the part as a target.

22. The computer readable medium as defined in claim 21, wherein the operation of performing a registration of the three-dimensional model to the range data further includes determining a composition of a first transformation T1 between data points on the three-dimensional model of the part and the range data, and an inverse of a second transformation T2 between the set of points in the range data having a high probability of corresponding to actual points on the three-dimensional model and data points on the three-dimensional model, to register the part with the three-dimensional model of the part; and wherein the operations further include the operation of associating gathered inspection data onto the three-dimensional model at the part pose to provide enhanced visualization of the inspection data.

23. The computer readable medium as defined in claim 21, wherein the set of points in the range data having a high probability of corresponding to actual points on the three-dimensional model are a set of points in the range data that are closest to corresponding points in the three-dimensional model as calculated using an iterative closest point algorithm.

24. The computer readable medium as defined in claim 23, wherein the transformation is a first transformation T1;

wherein the operation of performing a registration of the identified set of points in the range data having a high correspondence probability to the three-dimensional model includes determining a second transformation T2 between the set of points in the range data having a high probability of corresponding to actual points on the three-dimensional model of the part and data points on the three-dimensional model;

wherein the operation of aligning further includes determining a composition of the first transformation T1 and an inverse of the second transformation T2 to register the part with the three-dimensional model of the part; and wherein the operations further comprise mapping the inspection data into the three-dimensional model at the part pose responsive to registration of the part to the three-dimensional model of the part.

25. The computer readable medium as defined in claim 24, wherein the registration of the part with the three-dimensional model of the part provides a robust match independent of both an existence of outliers in the range data and missing data in the range data; and wherein the operation of aligning the three-dimensional model of the part to the measured pose of the part within the inspection cell is performed without pre-filtering the range data to remove outliers or a pre-accounting for missing data.

* * * * *